United States Patent [19]
Berthold et al.

[11] 4,137,331
[45] Jan. 30, 1979

[54] 3-PIPERIDINO-2-HYDROXYPROPOXY SUBSTITUTED-2-INDOLINONES

[75] Inventors: Richard Berthold; Franz Troxler, both of Bottmingen, Switzerland

[73] Assignee: Sandoz Ltd., Basel, Switzerland

[21] Appl. No.: 751,781

[22] Filed: Dec. 16, 1976

Related U.S. Application Data

[63] Continuation-in-part of Ser. No. 586,272, Jun. 12, 1975, abandoned.

[30] Foreign Application Priority Data

Jun. 19, 1974 [CH] Switzerland ............... 8380/74
Jun. 19, 1974 [CH] Switzerland ............... 8381/74
Sep. 23, 1976 [CH] Switzerland ............... 12063/76

[51] Int. Cl.$^2$ ............... C07D 401/12; A61K 31/445
[52] U.S. Cl. ............... 424/267; 544/294; 544/331; 546/273; 544/285; 546/112; 546/201; 260/239 E; 260/239 A; 260/325 R; 546/204; 260/326.5 CA
[58] Field of Search ............... 260/293.61; 424/267

[56] References Cited

U.S. PATENT DOCUMENTS

| | | | |
|---|---|---|---|
| 3,051,709 | 8/1962 | Shapiro et al. | 260/326.11 R |
| 3,153,613 | 10/1964 | Jones et al. | 260/293.51 |
| 3,699,123 | 10/1972 | Seemann et al. | 260/293.61 |
| 3,825,558 | 7/1974 | Seemann et al. | 260/325 |

FOREIGN PATENT DOCUMENTS 794,669  5/1973 Belgium.

*Primary Examiner*—Norma S. Milestone
*Attorney, Agent, or Firm*—Gerald D. Sharkin; Robert S. Honor; Thomas O. McGovern

[57] ABSTRACT

This invention provides new compounds of formula I, $$Het-O-CH_2-\overset{OH}{\underset{|}{CH}}-CH_2-R \qquad I$$

wherein
Het is a radical formed by removing one of the hydrogens from the phenyl ring of 2-indolinone or fluorenone, and
R is the group A, B, C or D, A: NH group attached to ring with -N B: NH group attached to ring with -N C: $-N\underset{}{\overset{(CH_2)_n}{\diagup}}\overset{X}{\underset{X'}{\diagdown}}$ D: $-N\underset{}{\overset{(CH_2)_{n'}}{\diagup}}$ wherein
n is the number 2 or 3,
n' is the number 1, 2, 3 or 4, and
X-X' is ethylene or vinylene,
wherein in group D each of the two C atoms adjacent to the N atom are identically substituted by hydrogen or by one or two alkyl groups of 1 to 4 carbon atoms useful as antiarrhythmic agents.

10 Claims, No Drawings

3-PIPERIDINO-2-HYDROXYPROPOXY SUBSTITUTED-2-INDOLINONES

This application is a continuation-in-part of my copending application Ser. No. 586,272 filed June 12, 1975, now abandoned.

The present invention relates to new heterocyclic compounds.

In accordance with the invention there are provided new compounds of formula I,

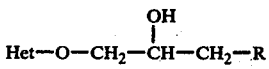

wherein
Het is a radical formed by removing one of the hydrogens from the phenyl ring of 2-indolinone or fluorenone, and
R is the group A, B, C or D,

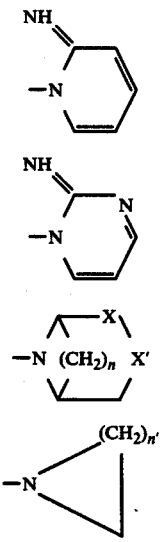

wherein
$n$ is the number 2 or 3,
$n'$ is the number 1, 2, 3 or 4, and
X–X' is ethylene or vinylene,
wherein in group D each of the two C atoms adjacent to the N atom are identically substituted by hydrogen or by one or two alkyl groups of 1 to 4 carbon atoms.

The propoxy side chain can be in the 4, 5, 6 or 7 position of the indolinone radical, preferably in the 4 position. The side chain may be in the 1, 2, 3 or 4 position of the fluorenone radical, conveniently in the 1, 2 or 4 position, especially in the 4 position.

When R is the group C, X–X' preferably signifies ethylene.

When R is the group D, $n'$ preferably signifies 3 or 4. The C atoms adjacent to the N atom are preferably alkylated, especially dialkylated. These alkyl substituents preferably contain 1 or 2, especially 1 carbon atom.

The radical R preferably signifies a tertiary amino group, the nitrogen atom thereof being linked with branched carbon atoms, e.g. a 2,2,5,5-tetramethylpyrrolidinyl or 2,2,6,6-tetramethylpiperidino radical.

Further, in accordance with the invention a compound of formula I may be obtained by a process comprising reacting a compound of formula IIa,

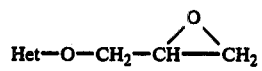

or of formula IIb,

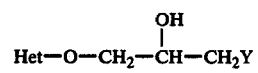

wherein Y is a leaving group, with a compound of formula III,

H — R            III wherein R is as defined above.

Acid addition salt forms may be obtained from the free base forms in known manner and vice versa. a suitable acid is hydrochloric acid.

The reaction of a compound of formula IIa or IIb with a compound of formula III may be effected in a manner analogous to the methods described for the production of known 3-amino-2-hydroxypropoxy compounds. Y in formula IIb is preferably the acid radical of a reactive ester especially halogen, preferably chlorine or bromine, or a group $R_2$—$SO_2$—O—, wherein $R_2$ is phenyl, tolyl or lower alkyl. The reaction is preferably effected in an inert organic solvent, e.g. in a cyclic or open chain ether such as dioxane or diethylene glycol dimethyl ether. An excess of the compound of formula III may optionally be used as solvent. The reaction may also be effected by fusion. The reaction temperature conveniently is between about room temperature and 200° C. The reaction time depends inter alia on the reaction temperature.

The compounds of formula I may be obtained from the reaction mixture and purified in accordance with known methods.

The starting materials of formulae IIa and IIb are known or may be produced in a manner analogous to known methods, using the corresponding hydroxyindole or hydroxyfluoren-9-one as starting material.

The compounds of formula III are known.

Insofar as the production of the required starting materials is not described, these are known or may be produced in accordance with known processes, or in a manner analogous to the processes described herein or to known processes.

In the following non-limitative Examples all temperatures are indicated in degrees Centigrade.

EXAMPLE 1

4-[2-hydroxy-3-(2,2,5,5-tetramethyl-1-pyrrolidinyl)-propoxy]-9-fluorenone 4 g of 4-(2,3-epoxypropoxy)-9-fluorenone are heated to 150° in an autoclave for 15 hours together with 4 g of 2,2,5,5-tetramethylpyrrolidine in 30 cc of dioxane. After cooling, the reaction mixture is concentrated by evaporation. The residue is taken up in ether and extracted with 2 N hydrochloric acid. The aqueous solution is made alkaline and thoroughly extracted with methylene chloride. The methylene chloride phase is concentrated by evaporation and the residue is crystallized from ethyl acetate/petroleum ether. The title compound has an M.P. of 137°–139°.

EXAMPLE 2

4-[3-(1-aziridinyl)-2-hydroxypropoxy]-9-fluorenone 4 g of 4-(2,3-epoxypropoxy)-9-fluorenone are allowed to stand at room temperature over night together with 15 cc of ethylene imine. The excess ethylene imine is removed by evaporation, the residue is taken up in ether and the solution is concentrated by evaporation until crystallization commences. The title compound has an M.P. of 113°–116°.

EXAMPLE 3

4-[2-hydroxy-3-(1,2-dihydro-2-imino-1-pyrimidinyl)-propoxy]-9-fluorenone 5 g of 4-(2,3-epoxypropoxy)-9-fluorenone and 3.8 g of 2-amino-pyrimidine are heated to 100° for 30 minutes. The melted material is taken up in ethyl acetate and is extracted with 2 N hydrochloric acid. The hydrochloride obtained as a resin is made alkaline and extracted with methylene chloride. The solvent is evaporated and the residue is crystallized from ethanol. M.P. 178°–179°.

The following compounds of formula I are obtained in analogous manner, using the corresponding starting materials of formulae IIa or IIb, wherein Y is chlorine, and III as starting materials:

-continued

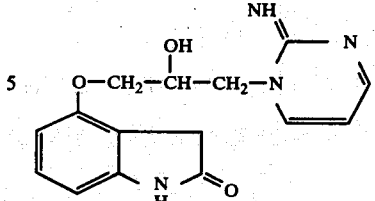

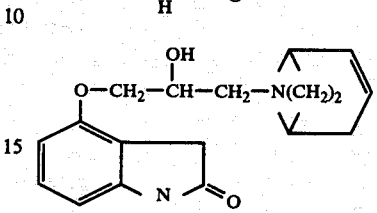

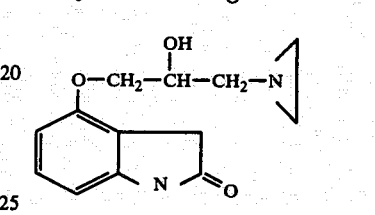

| Ex. Nr. | Analogous to Ex.Nr. | Het | Position of the side chain on the heterocycle | R | M.P. |
|---|---|---|---|---|---|
| 4 | 1 | 9-Fluorenone | 4 | 2,2,6,6-Tetramethylpiperidino | 113 – 116° |
| 5 | 1 | 9-Fluorenone | 4 | 8-Nortropanyl | 103 – 105° |
| 6 | 1 | 9-Fluorenone | 2 | 2,2,5,5-Tetramethyl-1-pyrrolidinyl | 235 – 237° (HCl)[a] |
| 7 | 1 | 2-Indolinone | 4 | 2,2,6,6-Tetramethylpiperidino | 177 – 178° |
| 8 | 1 | 2-Indolinone | 4 | 2,2,5,5-Tetramethyl-1-pyrrolidinyl | 164 – 166° |
| 9 | 1 | 2-Indolinone | 4 | 9-Azabicyclo[3.3.1]non-9-yl | 82° |
| 10 | 2 | 9-Fluorenone | 4 | 1-Pyrrolidinyl | 197 – 199° (HCl)[a] |
| 11 | 2 | 9-Fluorenone | 4 | 2,6-Dimethylpiperidino | 248 – 250° (HCl)[a] |
| 12 | 2 | 9-Fluorenone | 4 | 9-Azabicyclo[3.3.1]non-9-yl | 120 – 121° |
| 13 | 3 | 9-Fluorenone | 4 | 1,2-Dihydro-2-imino-1-pyridyl | 149 – 152° |
| 14 | 1 | 9-Fluorenone | 1 | 2,2,5,5-Tetramethyl-1-pyrrolidinyl | 210 – 212° (HCl)[a] |

| Ex. Nr. | Analogous to Ex.Nr. | Het | Position of the side chain on the heterocycle | R |
|---|---|---|---|---|
| 15 | 1 | 9-Fluorenone | 4 | Azabicyclo[3.3.1]non-2-en-9-yl |
| 16 | 1 | 2-Indolinone | 4 | Azabicyclo[3.3.1]non-2-en-9-yl |

[a]HCl = Hydrochloride

In analogous manner, the following compounds may be made:

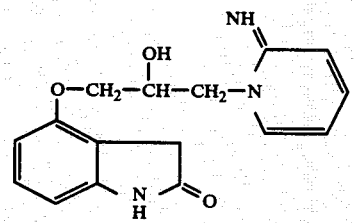

m.p. 112° (decomposition)

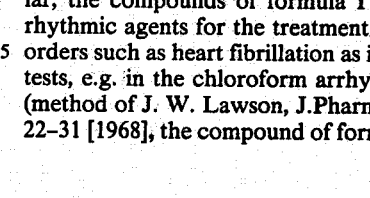

The compounds of formula I are useful because they possess pharmacological activity in animals. In particular, the compounds of formula I are useful as antiarrhythmic agents for the treatment of heart rhythm disorders such as heart fibrillation as indicated by standard tests, e.g. in the chloroform arrhythmia test with mice (method of J. W. Lawson, J.Pharm.Exper.Therap. 160, 22–31 [1968], the compound of formula I being administered i.p. at a dose of from about 0.1 to about 50 mg/kg animal body weight.

For the above mentioned use the dosage will, of course, vary depending on the compound employed, mode of administration and therapy desired. However, in general, satisfactory results are obtained when administered at a daily dosage of from 0.1 mg to about 50 mg per kg animal body weight, conveniently given in divided doses 2 to 4 times a day or in sustained release form. For the larger mammal, the total daily dosage is in the range from about 5 to about 400 mg, and dosage forms suitable for oral adminstration comprise from about 1 mg to about 200 mg of the compounds admixed with a solid or liquid pharmaceutical carrier of diluent.

Preferred compounds of formula I, wherein
Het has the side chain in the 4 position,
R is group D, wherein both ring carbons adjacent to the nitrogen atoms are dialkylated by alkyl of 1 to 4 carbon atoms, and
$n'$ is 3 or 4.

The Example 1 compound shows especially interesting activity.

In one group of compounds R is C or D. In a subgroup Het is derived from fluorenone. In another subgroup Het is derived from indolinone.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as mangnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

We claim:
1. A compound of the formula

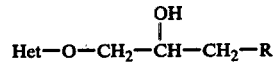

wherein
Het is 2-indolinone substituted in the 4-position by the

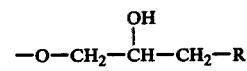

side chain and
R is

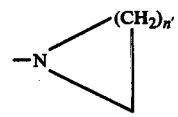

where
$n'$ is 4 and the carbon atoms adjacent to the N atom are identically dialkylated by two lower alkyls of 1 to 4 carbon atoms or
a pharmaceutically acceptable acid addition salt thereof.

2. A compound of claim 1, in which R is

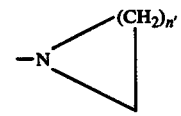

where $n'$ is 4 and the carbon atoms adjacent to the N atom are di-substituted with alkyl of 1 or 2 carbon atoms.

3. A compound of claim 1, wherein R is 2,2,6,6-Tetramethylpiperidino.

4. A pharmaceutical composition useful in the treatment of heart rhythm disorders comprising a therapeutically effective amount of a compound of claim 1 in association with a pharmaceutical carrier or diluent.

5. A pharmaceutical composition according to claim 4, useful in the treatment of heart rhythm disorder comprising 1 to 200 milligrams per unit dosage.

6. A pharmaceutical composition according to claim 4, wherein R is 2,2,6,6-tetramethylpiperidino.

7. A method of treating heart rhythm disorders in animals which comprises administering to an animal in need of such treatment a therapeutically effective amount of a compound of claim 1.

8. A method according to claim 7 in which 5 to 400 milligrams of the compound are administered daily.

9. A method according to claim 7 in which 1 to 200 milligrams of the compound are administered per unit dose.

10. A method according to claim 7 wherein R is 2,2,6,6-tetramethylpiperidino.